US012326431B2

(12) United States Patent
Miller et al.

(10) Patent No.: US 12,326,431 B2
(45) Date of Patent: Jun. 10, 2025

(54) GAS DETECTOR DEVICE CONTROL BASED UPON ACCESSORY IDENTIFICATION

(71) Applicant: MSA TECHNOLOGY, LLC, Cranberry Township, PA (US)

(72) Inventors: Daniel Miller, Cranberry Township, PA (US); Shane Kelleher, Glenshaw, PA (US); Minh Pham, Slippery Rock, PA (US); Anthony Bafile, Jeannette, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 277 days.

(21) Appl. No.: 18/083,491

(22) Filed: Dec. 17, 2022

(65) Prior Publication Data
US 2024/0201158 A1  Jun. 20, 2024

(51) Int. Cl.
*G01N 33/00* (2006.01)

(52) U.S. Cl.
CPC ..... *G01N 33/0073* (2013.01); *G01N 33/0009* (2013.01); *G01N 33/0016* (2013.01); *G01N 33/0031* (2013.01)

(58) Field of Classification Search
CPC .......... G01N 33/0009; G01N 33/0016; G01N 33/0031; G01N 33/0073
See application file for complete search history.

(56) References Cited

U.S. PATENT DOCUMENTS 5,162,725 A * 11/1992 Hodson ................. G01D 3/022
324/754.02
5,239,492 A    8/1993 Hartwig
(Continued)

FOREIGN PATENT DOCUMENTS

EP    2490193 B1    1/2014
EP    2778586 A1 *  9/2014 ............. F25D 23/04
(Continued)

OTHER PUBLICATIONS

Specification Sheet, iAssign technology, Industrial Scientific Corporation, https://www.indsci.com/en/gas-detectors/technology1/iassign/ 2021.
(Continued)

*Primary Examiner* — Justin N Olamit
(74) *Attorney, Agent, or Firm* — BARTONY & ASSOCIATES LLC (57) ABSTRACT

A gas detection device for detection of one or more gas analytes in an environment includes a housing including an inlet via which gas to be sampled from the environment enters the housing, a control system within the housing comprising a processor system and a memory system in communicative connection with the processor system, and one or more gas sensors within the housing in fluid connection with the inlet and in communicative connection with the control system. Each of the one or more gas sensors is independently responsive to one of the one or more gas analytes. The control system is configured to control flow rate of gas from the environment through an accessory device assembly including one or more accessory devices in fluid connection with the inlet on the basis of data for the accessory device assembly in fluid connection with the inlet.

20 Claims, 4 Drawing Sheets

(56) References Cited

U.S. PATENT DOCUMENTS

| | | | |
|---|---|---|---|
| 6,442,639 | B1 | 8/2002 | McElhattan |
| 6,837,095 | B2 * | 1/2005 | Sunshine ............ G01N 29/022 |
| | | | 73/23.3 |
| 7,530,255 | B2 | 5/2009 | Frank |
| 7,588,726 | B1 * | 9/2009 | Mouradian ........ G01N 33/0009 |
| | | | 702/22 |
| 8,215,150 | B2 | 7/2012 | Willett |
| 9,245,435 | B2 | 1/2016 | Boone |
| 9,410,940 | B2 | 8/2016 | Scheffler |
| 9,528,957 | B2 | 12/2016 | Scheffler |
| 9,562,873 | B2 | 2/2017 | Scheffler |
| 9,784,755 | B2 | 10/2017 | Scheffler |
| 9,952,125 | B2 * | 4/2018 | Caruso ............... G01N 33/0016 |
| 10,088,550 | B2 | 10/2018 | Johnson |
| 10,368,146 | B2 | 7/2019 | Potyrailo |
| 10,429,330 | B2 | 10/2019 | Le Neel |
| 10,551,396 | B2 | 2/2020 | Scheffler |
| 10,557,838 | B2 | 2/2020 | Worth |
| 10,578,573 | B2 | 3/2020 | Zanella, Sr. |
| 10,627,379 | B2 | 4/2020 | Zanella, Sr. |
| 10,725,003 | B2 | 7/2020 | Johnson |
| 10,782,274 | B2 | 9/2020 | Worth |
| 10,788,457 | B2 | 9/2020 | Miller |
| 10,788,458 | B2 | 9/2020 | Miller |
| 10,948,469 | B2 | 3/2021 | Zanella, Sr. |
| 10,983,103 | B2 | 4/2021 | Stokoe |
| 2016/0223436 | A1 | 8/2016 | Caruso |
| 2019/0064132 | A1 | 2/2019 | Poecher |
| 2019/0324005 | A1 | 10/2019 | Artiuch |
| 2019/0349360 | A1 | 11/2019 | Yeddula |
| 2020/0090297 | A1 | 3/2020 | Fabes |
| 2020/0103387 | A1 | 4/2020 | Brown |
| 2020/0124630 | A1 | 4/2020 | Scheffler |
| 2020/0363306 | A1 | 11/2020 | Sexton |
| 2020/0393405 | A1 | 12/2020 | Scheffler |
| 2021/0181135 | A1 | 6/2021 | Santoro, Jr. |
| 2022/0373568 | A1 | 11/2022 | Scheffler |
| 2023/0113553 | A1 | 4/2023 | Borneo |

FOREIGN PATENT DOCUMENTS

| | | |
|---|---|---|
| EP | 2770967 B1 | 5/2020 |
| WO | WO2015065390 A1 | 5/2015 |
| WO | WO2019152047 A1 | 8/2019 |
| WO | WO2020225796 A1 | 11/2020 |
| WO | WO2023059449 A1 | 4/2023 |
| WO | WO2014129389 | 6/2024 |

OTHER PUBLICATIONS

Sheet Using the Venti Pro Series with iAssign Technology, Industrial Scientific Corporation, https://www.indsci.com/en/gas-detectors/technology1/iassign/ 2021.

Star-Up Guide, https://www.indsci.com/en/gas-detectors/technology1/iassign/, Edition 3, Mar. 26, 2021.

U.S. Appl. No. 18/083,484, filed Dec. 17, 2022 of Daniel Miller et al.

* cited by examiner

GAS DETECTOR DEVICE CONTROL BASED UPON ACCESSORY IDENTIFICATION

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Gas detection devices (sometimes referred to as "instruments") include at least one gas sensor, electronic circuitry to drive the sensor, interpret its response, and display its response to the user, and a power supply. Such gas detection devices may include a variety of sensors for detecting gas analytes including, for example, electrochemical gas sensors and combustible gas sensors. See, for example, U.S. Pat. No. 9,784,755, the disclosure of which is incorporated herein by reference. Gas detection devices further include a housing to enclose and protect such components. Gas detection devices may be portable or fixed in position. Portable gas detection devices are typically powered by a rechargeable battery system. Portable gas detection devices are carried on the person of an authorized user or worker within a company/facility that may own or rent the portable gas detection device as an asset of the facility. Depending upon size and industry, a company/facility may, for example, have several, tens, or hundreds or more of such devices that are shared amongst a large, dynamic, and transitory workforce.

Accessories available in the gas detection market for use with, for example, gas detection devices, are numerous. Accessories, including pump probes, sampling lines of various lengths, materials, and use cases, as well as adapters, are typically used in pumped instrument applications where the instrument is being used as a tool for designation of gas levels in a specific area, and in many cases a specific gas or volatile organic compound (VOC). Currently, significant responsibility is placed on the end user to ensure proper use of such accessory devices in connection with a gas detection device.

Under current practice, the responsibility to select the correct accessory device or accessory device combinations (sometimes referred to as a stack) for an accessory device transport path or accessory device assembly for the sensor configuration of the instrument as well as to determine proper operation of the gas detection device in connection with selected accessory device(s) falls on the user. For example, after selection of accessory devices, a user must determine how much time to wait before a reading should be taken via a gas detection device or instrument to which the accessory device(s) are connected. The sample transport path includes the path through the accessory device(s) connected to the inlet and the transport path within the device from the inlet to the sensors of the device. The amount of time required for a sample from an environment being tested to fill or flood the accessory device path and reach the sensors of the gas detection device increases, for example, with increasing length of the accessory device transport path (predominantly as a function of the length of a sampling line accessory device). Other variables such as sampling line diameter also affect transit time of samples from a sampled environment. Likewise, different probes used in connection with sampling lines may result in different sample flow characteristics. A rule of thumb such as a defined period of delay, wait time, or sampling time (for example, a number of seconds) for each foot or meter of sampling line length may be used to assist in the determination.

A counter may be provided in certain device to assist the user in waiting for a sufficient period of time as the sampling transport path is being flooded for a specific, predetermined sampling transport path to prevent a user from ending the testing process too soon. The counter time length may, for example, depend upon sampling line length of a particular model of sampling line as identified by manual entry of a user.

Current practices, however, may result in a significant risk of user error as well as inefficiencies. It is desirable to develop improved technologies for use in connection with gas detection devices including sampling transport paths including one or more gas detection accessory devices.

SUMMARY

In one aspect, a gas detection device for detection of one or more gas analytes in an environment includes a housing including an inlet via which gas to be sampled from the environment enters the housing, a control system within the housing comprising a processor system and a memory system in communicative connection with the processor system, and one or more gas sensors within the housing in fluid connection with the inlet and in communicative connection with the control system. Each of the one or more gas sensors is independently responsive to one of the one or more gas analytes. The control system is configured to control flow rate of gas from the environment through an accessory device assembly including one or more accessory devices in fluid connection with the inlet on the basis of data for the accessory device assembly in fluid connection with the inlet. The gas detection device may further include a pump system including at least one pump in fluid connection with the inlet and in fluid connection with the one or more gas sensors.

In a number of embodiments, the gas detection device further includes a data transfer system in communicative connection with the control system via which the data for the accessory device assembly may be transmitted to the control system. In a number of embodiments, the data transfer system is configured for at least one of manual entry of data for the accessory device assembly by a user or to receive data transmitted from at least one communication device associated with the accessory device assembly. The data transfer system may be configured for manual entry of data for the accessory device assembly by a user and to receive data transmitted from at least one communication device associated with the accessory device assembly.

In a number of embodiments, the control system is configured to adjust speed of the at least one pump to alter flow rate of a gas sample from the environment to the one or more gas sensors on the basis of the data for the accessory device assembly in fluid connection with the inlet. The control system may, for example, be configured to adjust the speed of the at least one pump to a first speed, which may vary within a first range of speed, to provide a sample time of the one or more gas sensors within a range of predetermined response times. The control system may be configured to determine the first speed of the at least one pump such that the sample time of the one or more gas sensors is approximately a predetermined time regardless of the identification of the accessory device assembly in fluid connection with the inlet. In a number of embodiments, the control system is configured to increase the speed of the at least one pump to the first speed during transit of the gas sample to the one or more gas sensors and to decrease the speed of the at least one pump to a second speed, which may vary within a second range of speed, during measurement of one or more responses of at least one of the one or more gas sensors. The second speed may be determined to achieve a flow rate approximately equal to a calibration flow rate of the at least one pump during calibration of the one or more gas sensors with a test gas. The control system may, for example, be configured to determine the first speed at least in part based upon measured environmental conditions.

In a number of embodiments, the one or more gas sensors may be calibrated with a test gas at a plurality of pump speeds. In such embodiment, it may not be necessary to alter the pump speed (to a second speed, different from the first speed) during measurement of one or more responses of at least one of the one or more gas sensors.

In a number of embodiments, an accessory device identification system is in communicative connection with the control system. The accessory device identification system includes a database having stored therein data for a plurality of accessory device assemblies, including reference identification data therefor. The accessory device identification system is configured to identify the accessory device assembly identification data included in the data received via the data transfer system for the accessory device assembly in fluid connection with the inlet. The database may, for example, be stored in the memory system of the control system. The database may further have stored therein characterization data for the plurality of accessory device assemblies. The memory system may further include one or more algorithms stored thereon and executable by the processor system to control the at least one pump to adjust speed of the at least one pump to alter flow rate of a gas sample from the environment to the one or more gas sensors on the basis of the identification of the accessory device assembly.

In embodiments wherein the data transfer system is configured for manual entry of data for the accessory device assembly by a user, data entered manually may, for example, include characterization data for the accessory device assembly thereof. The memory system may further include one or more algorithms stored thereon and executable by the processor system to control the at least one pump to adjust speed of the at least one pump to alter flow rate of a gas sample from the environment to the one or more gas sensors on the basis of the characterization data of accessory device assembly in fluid connection with the inlet.

In another aspect, a method of operating a gas detection device for detection of one or more gas analytes in an environment includes controlling flow rate of gas from the environment through an accessory device assembly comprising one or more accessory devices in fluid connection with an inlet of the gas detection device via a control system of the gas detection device on the basis of data for the accessory device assembly in fluid connection with the inlet. The gas detection device may include a housing including the inlet via which gas to be sampled from the environment enters the housing and the control system within the housing. The control system may include a processor system and a memory system in communicative connection with the processor system. The gas detection device further includes one or more gas sensors within the housing in fluid connection with the inlet and in communicative connection with the control system. Each of the one or more gas sensors is independently responsive to one of the one or more gas analytes. The gas detection device may further include a pump system including at least one pump in fluid connection with the inlet and in fluid connection with the one or more gas sensors.

In a number of embodiments, the gas detection device further includes a data transfer system in communicative connection with the control system via which the data for the accessory device assembly may be transmitted to the control system. The data transfer system may be configured for at least one of manual entry of data for the accessory device assembly by a user or to receive data transmitted from at least one communication device associated with the accessory device assembly. In a number of embodiments, the data transfer system is configured for manual entry of data for the accessory device assembly by a user and to receive data transmitted from at least one communication device associated the accessory device assembly.

The method may further include adjusting (for example, via the control system) the speed of the at least one pump to alter flow rate of a gas sample from the environment to the one or more gas sensors on the basis of the data for the accessory device assembly in fluid connection with the inlet. In a number of embodiments, the method includes adjusting (for example, via the control system) the speed of the at least one pump to a first speed, which may vary within a first range of speed, to provide a response time of the one or more gas sensors within a range of predetermined response times. In a number of embodiments, the method includes determining (for example, via the control system) the first speed of the at least one pump such that the response time of the one or more gas sensors is approximately a predetermined time regardless of the identification of the accessory device in fluid connection with the inlet.

In a number of embodiments, the method includes increasing the speed of the at least one pump to the first speed during transit of the gas sample to the one or more gas sensors and decreasing the speed of the at least one pump to a second speed, which may vary within a second range of speed, during measurement of one or more responses of at least one of the one or more gas sensors. The second speed is determined to achieve a flow rate approximately equal to a calibration flow rate of the at least one pump during calibration of the one or more gas sensors with a test gas. The first speed may, for example be determined at least in part based upon measured environmental conditions.

In a number of embodiments, the one or more gas sensors may be calibrated with a test gas at a plurality of pump speeds. In such embodiment, it may not be necessary to alter the pump speed (to a second speed, different from the first speed) during measurement of one or more responses of at least one of the one or more gas sensors.

As described above, in a number of embodiments, an accessory device identification system is in communicative connection with the control system. The accessory device identification system includes a database having stored therein data for a plurality of accessory device assemblies, including reference identification data therefor. The accessory device identification system is configured to identify the accessory device assembly identification data included in the data received via the data transfer system for the accessory device assembly in fluid connection with the inlet. The database may, for example, be stored in the memory system of the control system. The database may further have stored therein characterization data for the plurality of accessory device assemblies. The memory system may further include one or more algorithms stored thereon and executable by the processor system to control the at least one pump to adjust speed of the at least one pump to alter flow rate of a gas sample from the environment to the one or more gas sensors on the basis of the identification of the accessory device assembly.

As also describe above, in embodiments wherein the data transfer system is configured for manual entry of data for the accessory device assembly by a user, data entered manually may, for example, include characterization data for the accessory device assembly thereof. The memory system may further include one or more algorithms stored thereon and executable by the processor system to control the at least one pump to adjust speed of the at least one pump to alter flow rate of a gas sample from the environment to the one or more gas sensors on the basis of the characterization data of accessory device assembly in fluid connection with the inlet.

In another aspect, a method of detecting one or more gas analytes in an environment includes controlling flow rate of gas from the environment through an accessory device assembly comprising one or more accessory devices placed in fluid connection with an inlet of a gas detection device on the basis of data for the accessory device assembly received via a data transfer system of the gas detection device. The gas detection device further including one or more sensors in fluid connection with the inlet, wherein each of the one or more gas sensors is independently responsive to one of the one or more gas analytes.

The devices, systems, and methods hereof, along with the attributes and attendant advantages thereof, will best be appreciated and understood in view of the following detailed description taken in conjunction with the accompanying drawings.

DETAILED DESCRIPTION

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an accessory device" includes a plurality of such accessory devices and equivalents thereof known to those skilled in the art, and so forth, and reference to "the accessory device" is a reference to one or more such accessory devices and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software, or combinations of each to perform a function(s) or an action(s). For example, based on a desired feature or need. a circuit may include a software-controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software-controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random-access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

As used herein, the term "personal communications device" refers to a portable or mobile device which includes a communication system, a processor system, a user interface system (for example, a visual feedback system including a touchscreen or other display, an auditory feedback system, and a tactile feedback system, a user input system etc.) and an operating system capable of running general-purpose applications. Examples of personal communications devices include, but are not limited to, smartphones, tablet computer and custom devices. As used herein, the term "tablet computer" or tablet, refers to a mobile computer with a communication system, a processor system, at least one user interface as described above (typically including a touchscreen display), and an operating system capable of running general-purpose applications in a single unit. As used herein, the term "smartphone" refers to a cellular telephone including a processor system, at least one user interface as described above (typically including a touchscreen display), and an operating system capable of running general-purpose applications. Such personal communication devices are typically powered by rechargeable batteries and are housed as a single, mobile unit. Moreover, in a number of embodiments personal communications devices are able accept input directly into a touchscreen (as opposed to requiring a keyboard and/or a mouse). Personal communications devices as typically provide for internet access through cellular networks and/or wireless internet access points connected to routers. A number of representative embodiments of systems and/or methods hereof are discussed in connection with the user of a smartphone as the personal communication instrument or device is described as a component of a system which includes.

As used herein, the term "database" refers an organized collection of structured information, or data, typically stored electronically in a memory system of a computer system. As used herein, the term "approximately" when used in connection with a value means within 10%, within 5%, or within 2% unless otherwise indicated herein or otherwise clearly contraindicated by the text.

In a number of embodiments of devices, systems, and methods hereof, a gas detection device includes a housing including, a control system (for example, including a processor system and a memory system in communicative connection with the processor system), one or more gas sensors within the housing in fluid connection with the inlet and in communicative connection with the control system. The control system is configured to control flow rate of gas from the environment through an accessory device assembly including one or more accessory devices placed in fluid connection with the inlet on the basis of data for the one or more accessory devices in fluid connection with the inlet. The gas detection device may further include a data input/output or data transfer system in communicative connection with the control system via which data for the accessory device assembly (including the one or more accessory devices) may be transferred to the control system. The gas detection device may further include a pump system including at least one pump in fluid connection with the inlet and in fluid connection with the one or more gas sensors. Pump speed of the pump may be controlled by the control system to control flow rate through the one or more accessory devices. In a number of embodiments, the data transfer system is configured for at least one of manual entry of data for the accessory device assembly by a user or to receive data transmitted from a communication device or devices associated with the accessory device assembly (for example, independently from a separate communication device associated with each of the one of the one or more accessory devices or with a single communication device associated with a combination of accessory devices which make up the accessory device assembly).

In a number of embodiments, an accessory device identification system may be in communicative connection with the control system of the gas detection device. The accessory identification system includes a database having stored therein data for each of a plurality of accessory devices and/or for each of a plurality of combinations or stacks accessory devices including reference identification data therefor. The plurality of accessory devices and/or the plurality of combinations of accessory devices may include the one or more accessory devices associated with the gas detection device (that is, attached to or to be attached to the inlet of the gas detection device). The accessory device identification system is configured to identify the one or more accessory devices and/or combinations thereof from identification data included in the data for the one or more accessory devices in fluid connection with the inlet received via the data input system.

The control system is configured to control operation of the pump system on the basis of characterization data associated with the accessory device assembly which includes one or more accessory devices in fluid connection with the inlet. As used herein, "characterization data" includes any data associated with an accessory device assembly for analysis thereof, including data that can be used in determining operational parameters of a gas detection device in operative connection with the accessory device assembly. As discussed further below, characterization data may, for example, include physical parameter data for a particular accessory device or for a combination of accessory devices of an accessory device assembly. Characterization data or variables relevant to characterizing flow through an accessory device transport path or accessory device assembly (and in controlling flow through that path) include, for example, sample line length, sample line diameter, and probe characteristics. Probe filters may, for example, have a significant effect upon flow. Characterization data may also or alternatively include operational parameters (for operation of the gas detection device via the control system/electronic circuitry thereof) associated with an accessory device assembly including an accessory device or a combination of accessory devices.

The data transfer system may provide for manual entry of identification data for one or more accessories in case in which reference identification and characterization data for such accessory devices is present in the database. Further, the data transfer system may provide for manual entry of characterization data, for example, in case when there is no data for one or more accessory devices in the database.

In representative embodiments discussed herein, a portable gas detection device hereof is described as being in communicative connection with a network or grid of components, devices or systems to, for example, provide software-based assistance in managing the gas detection instrument or device or a plurality/fleet thereof. As clear to one skilled in the art, however, the devices, systems and methods hereof may be operated independently of such a network or grid.

Figures 1A, 1B:
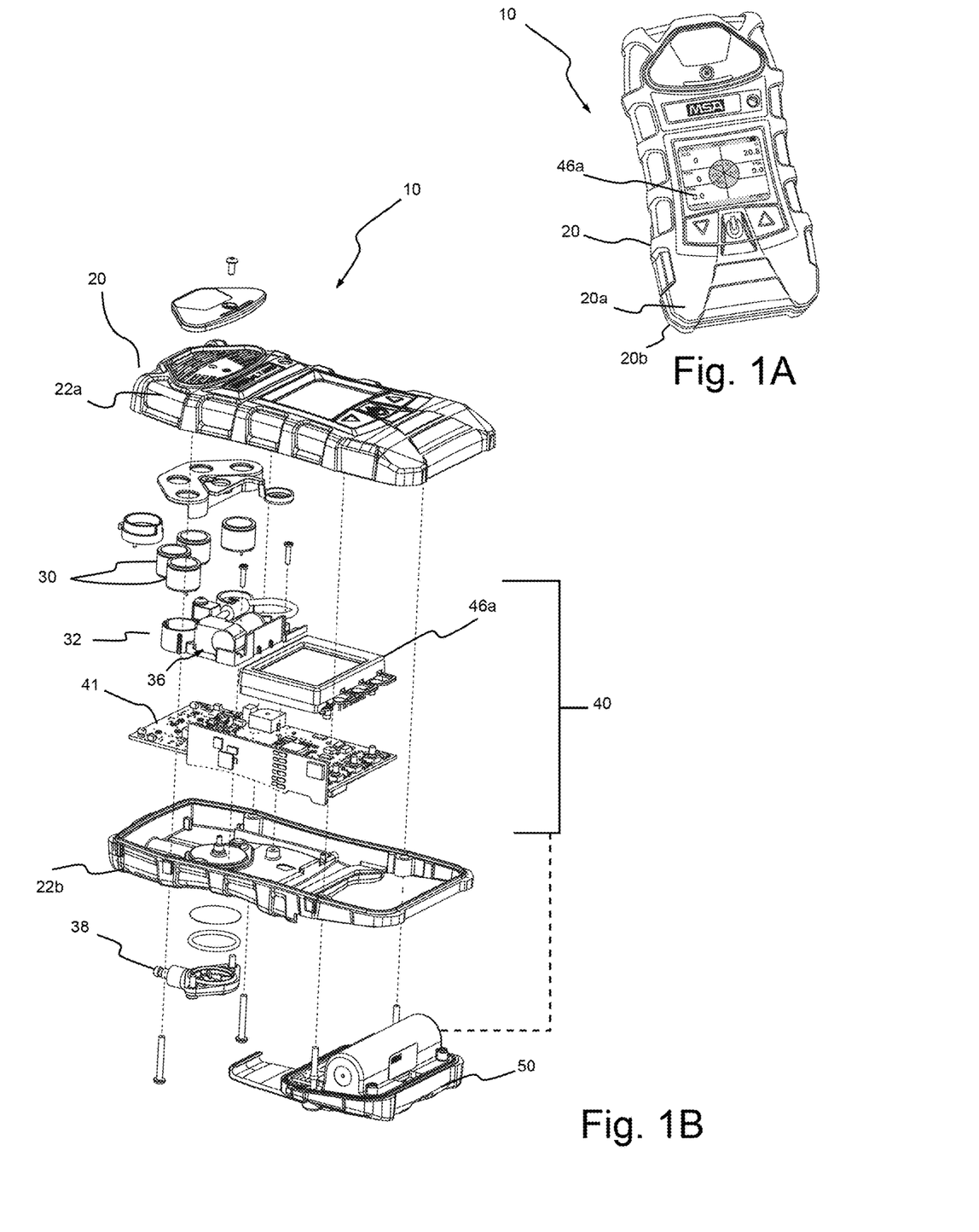
FIG. 1A illustrates a front isometric view of a representative embodiment of a gas detection instrument, device or detector for use herein.
FIG. 1B illustrates an isometric, exploded or disassembled view of the gas detection instrument of FIG. 1A.
Figure 2:
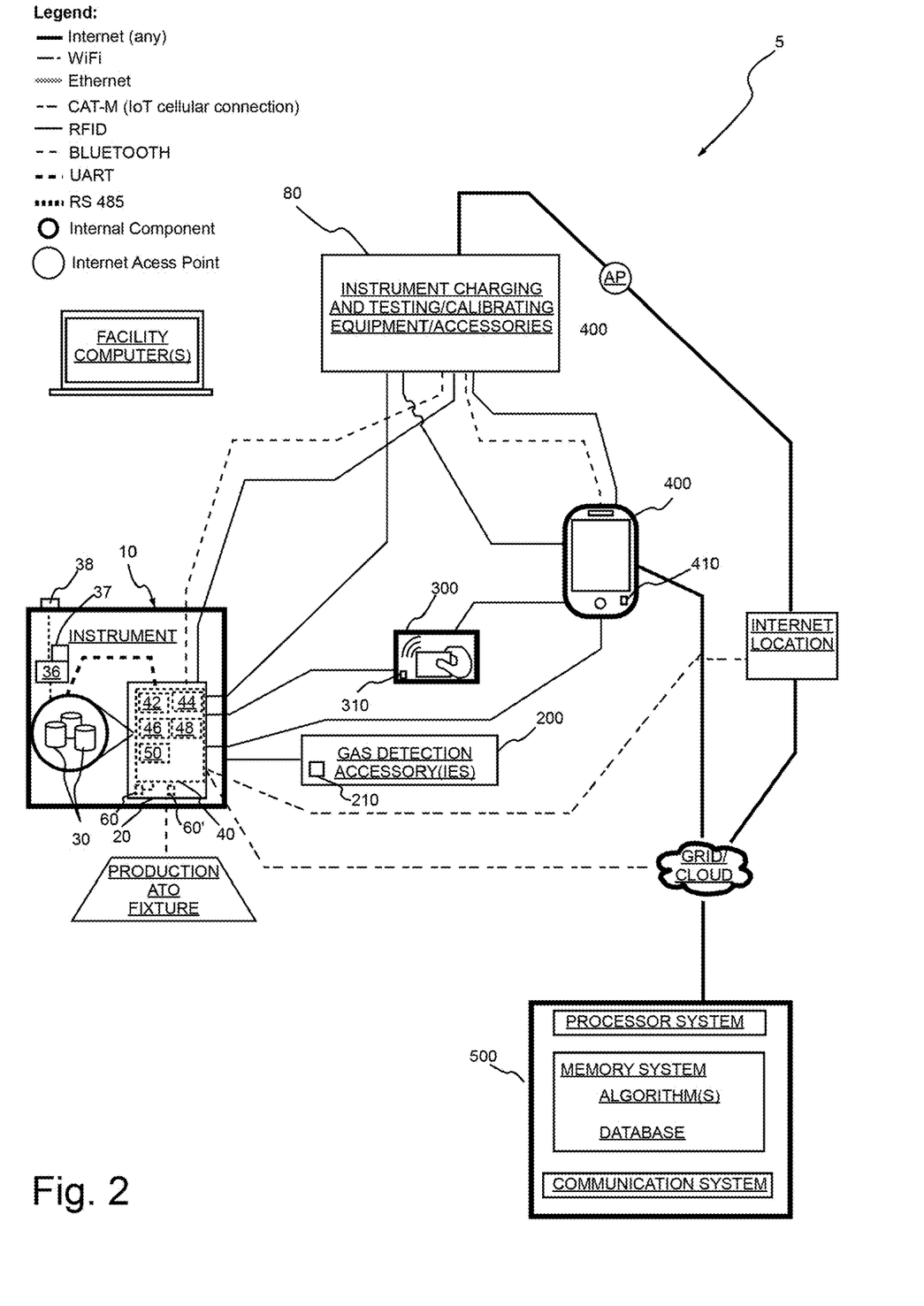
FIG. 2 illustrates schematically communication in an embodiment of an instrument management grid or network hereof.
Figure 3A:
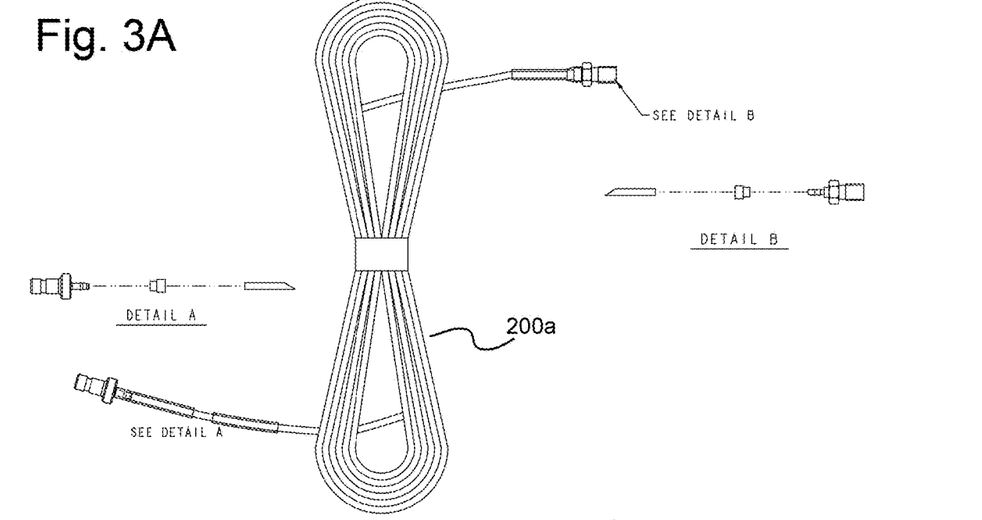
FIG. 3A illustrates an embodiment of a sampling line accessory for use with, for example, the gas detection instrument of FIG. 1A.
Figure 3B:
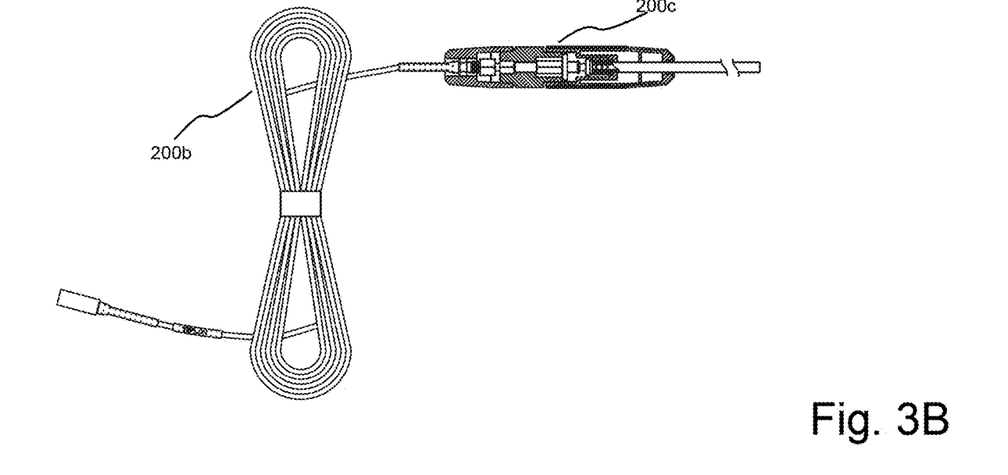
FIG. 3B illustrates an embodiment of a sampling line and a connected probe accessory for use with, for example, the gas detection instrument of FIG. 1A.
Figure 3C:
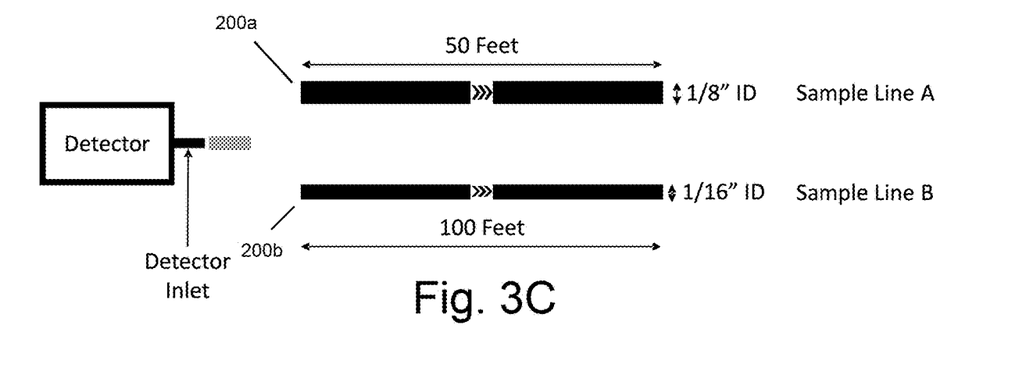
FIG. 3C illustrates schematically different line lengths and diameters of sampling lines for use in connection with, for example, the gas detection instrument of FIG. 1A.
Figure 4A:
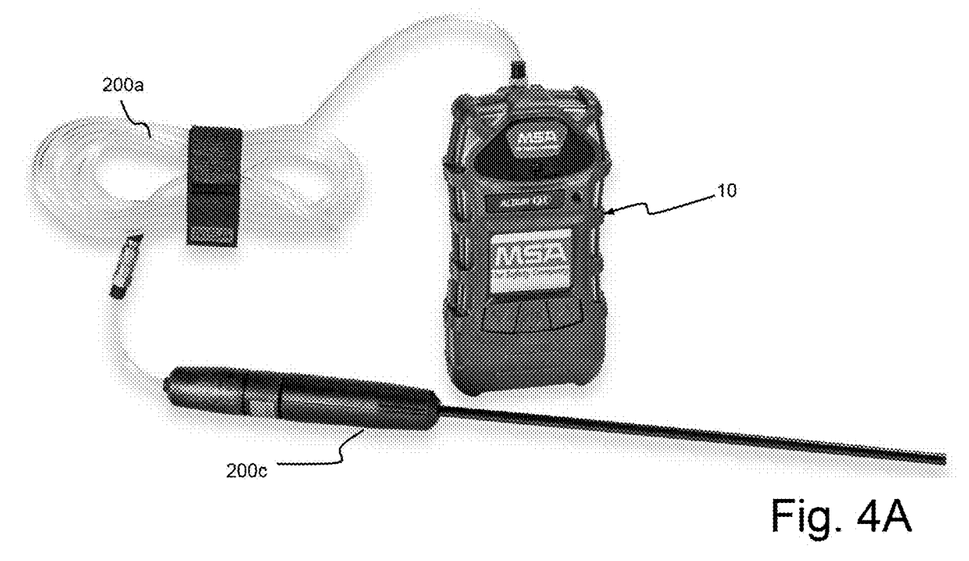
FIG. 4A illustrates a system including the gas detection instrument of FIG. 1A, a sampling line, and a probe.
Figure 4B:
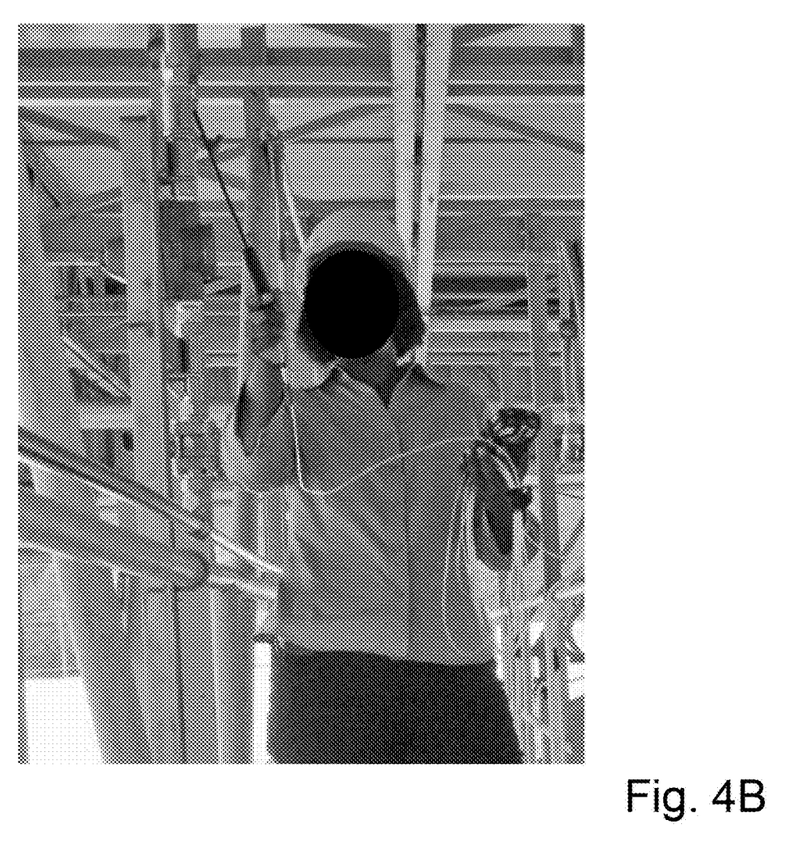
FIG. 4B illustrates use of the system of FIG. 4A in a facility.

FIGS. 1A, 1B and 2 illustrates an embodiment of a portable instrument, detector device, or device 10 including a housing 20 formed from housing sections 22a and 22b to encompass one or more sensors 30 which may be seated within a sensor bracket 32. Bracket 32 also supports a pump system 36 in fluid connection with inlet 38. Each sensor is operable to detect the presence of an analyte. Sensors 30 are placed in connection with an environment to be tested via inlet 38.

Device 10 further includes electronic circuitry 40 including a controller or control system to control operation of device or instrument 10 and to analyze or interpret the responses of the sensor(s) 30. As illustrated schematically in FIG. 2, the control system may, for example, include a processor system 42 (for example, including one or more microprocessors) in operative connection with a memory system 44. As illustrated in FIG. 1B, elements of electronic circuitry can be incorporated in one or more printed circuit boards 41. One or more software algorithms may be stored in memory system 44 which is/are executable by processor system 42 to control/operate device 10 including, for example, data measurement/acquisition, analysis, device accessory identification and analysis as described herein, communication etc. A user interface system 46 (including, for example, a display 46a (see FIG. 1B), a speaker, a tactile system, various data input/output systems, etc.) may also be placed in operative or communicative connection with processor system 42. A communication system 48 is in operative or communicative connection with processor system 42 for wired and/or wireless communication to other devices/systems to achieve, for example, data input/output or transfer. A power source 50 (for example, a battery system including one or more lithium batteries) provides power for electronic circuitry 40. Gas sensor(s) 30 may, for example, be placed in operative or communicative connection with electronic circuitry 40 via Universal Asynchronous Receive/Transmitter or UART protocol which may, for example, be a part of integrated circuit (IC) used for serial communications over a serial port.

As, for example, described in U.S. patent application Ser. No. 17/496,420, the disclosure of which is incorporated herein by reference, gas detection instrument or device 10 may, in a number of embodiments, be in communicative connection with a network or grid which, for example, provides software-based assistance in managing a gas detection instrument or a plurality/fleet of gas detection instruments and accessories therefor (such as the Grid Fleet Manager available from Safety io of Cranberry Township, PA). Such a software-based system or grid 500 (see FIG. 2) may, for example, be in communicative connection with or implemented upon one or more computers/networks located at a facility and/or located remotely as part of an overall network or system 5. The devices, systems and methods hereof for control of operation of instrument or device 10 hereof may be fully integrated into a gas detection instrument or device 10 which may or may not be in operative connection or integrated with such a networked system. However, in other embodiments, various components or functionalities of the devices, systems, and methods hereof may be distributed among one or more other devices of a networked system such as system 5.

In a number of embodiments, software-based management system 500 is a cloud-based system in communicative connection with one or computers/networks and/or devices located at a facility. For example, in a number of embodiments, management system 500 is a remote, cloud-based system via which a particular facility may create an account to enable use of the software-based management system to assist the facility in consolidating and streamlining gas detection related activities in a single source, thereby facilitating information access, instrument/accessory compliance, risk assessment, and worker compliance. A cloud-based system may also facilitate sharing of information or data with a remote location (for example, of a manufacturer of gas detection instruments and accessories therefor) to, for example, further process data and/or provide enhanced functionality.

Management system 500, which may, for example, include a computer or a plurality of interconnected/networked computers, provides a centralized destination for managing/monitoring the facility's fleet of gas detection instruments and accessories therefor. In a number of embodiments, management system 500 is accessible, for example, via account login from facility computers, mobile devices etc. One may, for example, provide real-time notifications, instrument configuration, fleet management and relevant contextual reporting via system/grid. Management system 500 may, for example, execute a web-based application to transmit data to system 5 and received data from system 5.

FIG. 2 illustrates an embodiment of a system 5 hereof for an entity or facility including portable gas detection devices instrument(s) 10 as well as associated equipment or accessory devices therefor. In the illustrated embodiment, system 5 includes a system 80 for instrument charging and testing which may, for example, include one or more single- and/or multiple-unit chargers, calibration stands, and gas cylinder holders to operatively connect to gas cylinders. The interaction of instrument(s) 10 with system 80 to achieve assignment to and de-assignment from particular users is, for example, described in U.S. patent application Ser. No. 17/496,420. Various wired and/or wireless communication protocols as illustrated in the representative embodiment of FIG. 2 may be used in system 5 to communicate data between facility devices/systems as well as to communicate data between facility device/systems and supervisory or management system 500. Supervisory or management system 500 includes one or more processor systems programmed with one or more algorithms stored in a memory system as, for example, described herein and in U.S. patent application Ser. No. 17/496,420.

In the illustrated embodiment, portable gas detection device 10 includes a data transfer system or data input/output system in communicative connection with the control system thereof as described above. As known in the computer arts such a data system or data transfer system may, for example, include one or more communication devices and/or user interface devices which are operable to or configured to communicate data/information to/from gas detection device 10. As described above, the data system may be configured for at least one of manual entry of data for one or more accessory devices to be attached to device 10 or to receive data for one or more accessory devices 200 data in an automated or semiautomated manner. Automated or semiautomated data transfer in, for example, identification of one or more accessory devices 200 via an identification system is described in U.S. patent application Ser. No. 18/083,484, filed Dec. 17, 2022, the disclosure of which is incorporated herein by reference. A communication device may, for example, be integrated into or be in operative/communicative connection with communication system 48 and/or electronic circuitry 40. The communication device or devices communicate with a corresponding or cooperating communication device of gas detection accessory device(s) 200 to be used with device 10. In a number of embodiments, the proximity of the instrument or device 10 and the corresponding communication device 210 of a gas detection accessory device 200 may initiate communication/transmission of data/information without user intervention beyond taking some action to effect proximity. The communication device(s) of device 10 may communicate with the corresponding communication device 210 or identifier of gas detection accessory 200 via a wired (for example, through contact of one or more conductive contact elements) or a wireless manner (for example, via electromagnetic waves such as radio waves, via hall effect switches or via an optical reading methodology such as a bar code reader). In the case that an accessory device combination is used in an assembly attached to inlet 38, each accessory device 200 in the combination may be identified sequentially in a number of embodiments. For example, each accessory device 200 may include a separate RFID tag (or other proximity device) and be brought into proximity with device 10 sequentially to identify all accessory devices 200 in the combination. In other embodiments, a combination or stack of accessory items to be used in an assembly attached to inlet 38 may, for example, be provided a kit and a single RFID tag (or other proximity device) may be associated with the combination to transmit or provide data including identification data for the combination or stack of the assembly.

Device 10 may also or alternatively monitor (via, for example, one or more sensors) one or more operational variables or parameters such a pump motor back EMF, pressure (measured, for example, via a pressure transducer), pulse width modulation (PWM) parameters, etc. to identify an accessory device assembly based on stored data for such operational variables or parameters. Additionally, time and environmental conditions such as temperature and relative humidity may be measured and tracked for identification and/or analysis. Environmental conditions may, for example, affect measured operational variables or parameters such a pump motor back EMF, pressure, and/or pulse width modulation parameters. Pump motor back EMF (and/or pressure, PWM parameters, or other parameters) may, for example, be measured at startup for changes in motor pull-in torque as a result of pressure-drop across one or more accessory devices (for example, a sampling line etc.). Such changes in operational parameters measured in start-up are characteristic of an attached accessory device assembly. Detection of one or more operational parameters for accessory device assembly identification may, for example, be used to decrease user interactions steps required in the identification process (as compared to, for example, use of a proximity-based communication system). Manual entry of data for accessory device assembly or the one or more accessory devices thereof may, for example, be achieved via interface system 46.

Moreover, operational variables or parameters such as back EMF, pressure, and/or pulse width modulation parameters may be used to check for proper attachment and/or functioning of identified accessory devices 200 or combinations thereof. For example, a leak in the accessory device transport path or accessory device path may result in a higher back EMF or pressure than stored in memory for the identified accessory device(s) 200. A blockage or occlusion in the accessory transport line (for example, a blocked filter) may result in a lower back EMF or pressure than stored in memory for the identified accessory device(s) 200. Data for determination of proper attachment and/or functioning of an accessory device may be stored in a database hereof and may overlap partially or completely with stored data used in device accessory identification via a device operational parameter.

As described in U.S. patent application Ser. No. 18/083,484, the accessory device identification system may include a database, which may be stored in memory system 44. The database has stored therein data for at least one of a plurality of accessory devices or a plurality of combinations of accessory devices and/or combinations thereof, including reference identification data and corresponding characterization data associated therewith. Such data may be supplemented and/or updated on a regular basis as necessary to, for example, add various accessory devices or combinations thereof or update data for existing accessory devices or combinations thereof. The accessory device identification system is further configured to identify one or more accessory devices 200 and/or combinations thereof by comparing the identification data received for each of accessory devices 200 (or entered manually) with the reference identification data of stored for the plurality of accessory devices and/or the plurality of combinations of accessory devices.

Examples of wireless data communication devices suitable for use herein to communication data when in proximity include, but are not limited to, radio-frequency identification (RFID) devices and near field communication (NFC) devices. In a number of representative embodiments discussed herein, the communication device of instrument 10 includes an RFID device, reader, or chip 60 which is in operative or communicative connection with electronic circuitry 40. As known in the art, RFID systems utilize electromagnetic energy/fields to wirelessly communicate with RFID tags which are associated with objects. RFID tags include a microchip or integrated circuit to store and process information. The integrated circuit further modulates and demodulates radio-frequency or RF signals. The RFID tag further includes an antenna to receive and transmit the signal over relatively short distances. Data/information of the tag is stored in a non-volatile memory. Either fixed or programmable logic is provided for processing the transmission and sensor data.

As also illustrated in the embodiment of system 5 of FIG. 2, information associated with individual user data can be substantially automatically transferred via for example a card 300 (or other object or item carried on the person of, including worn by, the user) including a communication device such as an RFID device/tag 310. In that regard, individual user data (associated with a user such as identity, entity affiliation etc.) can be transmitted to RFID device/reader 60 of device 10 upon placing card 300 in proximity to RFID reader 60. In a number of embodiments, the data transmitted from tag includes the UUID (universally unique identifier) or other unique identification information of RFID device/tag 310. The UUID or other unique identification information of RFID tag 310 is associated with the information of the individual user in the database of management system 500. In that regard, upon removal of device 10 from a bay of charger of system 80 by a user/worker, the user's information is read (for example, from card 300 when in proximity to device 10) by device 10 and device 10 is designated as assigned to the user. Device 10 may remain assigned to the user until instrument 10 is placed in one of the bays of a validated charger of system 80 and a de-assignment occurs.

In addition to transfer of information form card 300 to device 10, information can be transferred from card 300 of the user and/or another device of system 5 to a personal communication device 400 of the user as illustrated in FIG. 2. Personal communication device 400 may, for example, be a near field communication NFC/RFID enabled device as represented schematically by element 410 in FIG. 2. Furthermore, personal communication device 400 may receive data from device 10 via RFID communication from an RFID tag 60' or other communication instrument of device 10. Personal communication device 400 (for example, a smartphone) may, for example, be used in management of RFID tag and associating data with such tags in management system 500. In that regard, an application or app can be downloaded (for example, from management system 500) via which personal communication device 400 can be used to, for example, set up/program RFID tags or other communication devices to, for example, associate personal/identity information or data of the associated user with the UUID of RFID tag 310 or other communication device of card 300. A mobile app on personal communication device 400 may, for example, be used to download a workforce roster from management system 500. Placing personal communication device 400 into proximity with card 300 can be used to achieve pairing, for example, in the cloud.

As set forth above, number of accessory devices are desirable or required for the use of portable gas detection instruments of a gas monitoring system of an entity (for example, a company or facility). As, for example, illustrated in FIGS. 3A through 4B, portable instruments such as instrument 10 are often used in connection with various accessory devices including sampling lines and probes through which an environmental sample is pumped to the sensor via a pump system 36 in fluid connection with inlet 38 (see FIG. 1B). Tables 1 through 8 below, in connection with FIGS. 3A through 4B provide some insight into various choices of sampling lines available from a single supplier (MSA Safety Incorporated of Cranberry Township, Pennsylvania).

TABLE 1

| Sampling Lines with Quick Connectors | | | |
|---|---|---|---|
| Product No. | Material | Length | Diameter |
| 10040662 | Polyurethane, Coiled | 5 ft | 1/16" |
| 10040663 | Polyurethane | 15 ft | |
| 10040664 | Polyurethane | 25 ft | |
| 10040665 | Polyurethane | 10 ft | |
| 10040666 | Polyurethane | 5 ft | |

TABLE 1-continued

| Sampling Lines with Quick Connectors | | | |
|---|---|---|---|
| Product No. | Material | Length | Diameter |
| 10040667 | Polyurethane, Coiled | 3 ft | |
| 10049057 | Teflon | 25 ft | |
| 10049058 | Teflon | 10 ft | |

TABLE 2

| Sampling lines with threaded connectors | | | |
|---|---|---|---|
| Product No. | Material | Length | Diameter |
| 710217 | Polyurethane | 3 ft | 1/16" |
| 497332 | Polyurethane | 5 ft | |
| 497333 | Polyurethane | 10 ft | |
| 497334 | Polyurethane | 15 ft | |
| 497335 | Polyurethane | 25 ft | |
| 800972 Brass Bulkhead | Teflon | 5 ft | |
| 100745 Stainless Steel Bulkhead | Teflon | 5 ft | |
| 100181 | Polyurethane, Coiled | 3 ft | |
| 100473 | Polyurethane | 50 ft | |
| 100473 | Polyurethane | 25 ft | |
| 100537 | Polyurethane | 5 ft | |
| 100537 | Polyurethane | 10 ft | |

TABLE 3

| Conductive Sampling Lines | | |
|---|---|---|
| Product No. | Material | Length |
| 10103188 | Polyurethane, Conductive | 1.5 m |
| 10103189 | Polyurethane, Conductive | 3 m |
| 10103190 | Polyurethane, Conductive | 5.0 m |

TABLE 4

| Sampling Probes with Quick Connects | | |
|---|---|---|
| Product No. | Material | Length |
| 10042621 | PEEK | 1 ft |
| 10042622 | PEEK | 3 ft |

TABLE 5

| Probe and Sampling Lines with Quick Connects | | | |
|---|---|---|---|
| Product No. | Material | Length | Diameter |
| 10105210 | Polyurethane, Coiled | 5 ft | 1/16" |
| 10105251 | Polyurethane | 5 ft | |
| 10105838 | Teflon | 10 ft | |

TABLE 6

ALTAIR Hand Probe, Clear

| Product No. | Material | Length |
|---|---|---|
| 10150844 | Hand Probe | 1 ft |
| 10153041 | Hand Probe | 1 ft |
| 10165190 | Hand Probe, w/Quick Connect | 1 ft |

TABLE 7

Conductive Sampling Probe

| Product No. | Material | Length |
|---|---|---|
| 10103191 | Sampling Probe | 1 ft |

TABLE 8

Dilution Tubes and Adapters

| Product No. | Description |
|---|---|
| 813514 | Dilution Tube |
| 100490 | Quick Connect |
| 100490 | Quick Connect |
| 10161775 | Quick Connector |
| 10053294 | Fitting, QCK Disconnect |
| 10151722 | Quick Disconnect |

Characterization data associated with an accessory device assembly may, for example, include the data provided in any one of Table 1 through 8 and device operational parameters. Such, stored characterization data may depend on or include conditions of use (including for example, location/mode of use, environmental conditions, user etc.). Table 9 below sets forth representative data for accessory device assembly identification and representative data for characterization/analysis for two representative accessory device assemblies (wherein each such assembly includes a sampling line only, with no sampling probe or adapters). Assembly A includes a ⅛ inch diameter sampling tube of 10 feet in length. Assembly B includes a 1/16 inch diameter sampling tube of 50 feet in length. Additional characterization data may be provided as described herein and depending upon desired analysis/operational parameters for the use of various accessory device assemblies.

TABLE 9

| Accessory | | | | | | | Look-Up Table limits established via Characterization Testing of Accessory Assembly | |
|---|---|---|---|---|---|---|---|---|
| Assembly ID (e.g. UUID) | Temp. (° C.) | Relative Humidity (%) | PWM (%) | Back Emf (V) | Press. (PSI) | Flow Rate (LPM) | Minimum Pressure (PSI) | Maximum Pressure (PSI) |
| Assembly A | T | RH | $X_A$ | $Y_A$ | $P_A$ | $Z_A$ | $P_{A1}$ | $P_{A2}$ |
| Assembly B | T | RH | $X_B$ | $Y_B$ | $P_B$ | $Z_B$ | $P_{B1}$ | $P_{B2}$ |

Automated or partially automated identification of one or more device accessories 200 and analysis/matching of such accessory devices 200 and combinations or stacks thereof via an accessory device identification system may be used to reduce the burden upon the user in selecting an accessory device 200 or combination/stacks of accessory device 200 for use with device 10 as described in U.S. patent application Ser. No. 18/083,484 as well as in controlling device 10 based upon the identified accessories device(s) and associated characterization data. However, as described above, manual entry of data (identification data and/or characterization data) for one or more device accessories 200 or accessory device combinations of an accessory device assembly used in connection with gas detection device 200 may be used in the devices, systems, and methods hereof. Gas detection devices 10 hereof may integrate (either fully or partially) or be in operative/communicative connection with an accessory device identification system which is configured for at least one of manual entry of data for the one or more accessory devices by a user or for identification of the one or more accessory devices from transmitted or sensed identification data received for each of one or more accessory devices.

In current practice, gas detection devices including a pump system to draw sample gas to the sensor of the device are calibrated and operated at predetermined, standard range of pump speed regardless of the identification, nature, and/or properties of one or more accessory devices attached to the gas detection device. Upon identification/characterization of accessory devices 200, device 10 hereof (either operating alone or in combination with one or more other components of system 5) may, for example, determine a wait time or sample time required for the standard range of pump speed based on the saved or entered characteristics of the identified accessory device 200 or combinations thereof. Additionally or alternatively, the electronic circuitry/control system is configured to control operation of the device 10 to control the flow rate of gas from the environment to be sampled through the sample transport path by, for example, control of pump speed (including the accessory device path and the path between inlet 38 and one or more sensors 30) to change pump speed for a first speed, that may vary within a first range of pump speeds, that is outside of the standard range of pump speed.

In that regard, pump system 36 may include at least one pump in fluid connection with inlet 38 and in fluid connection with gas sensors 30. As described above, pumps of portable gas detection devices are currently operated within a predetermined range of speed regardless of the nature or properties of any attached accessory device(s) 200. Generally, a gas detection device is calibrated using a test gas (including a known concentration of one or more analyte gases or simulants therefor) within the above-described standard range of pump speed and associated flow rate which is used in operating the gas detection device. In a number of embodiments, the control system hereof is configured to adjust speed of the a pump of pump system 36 to alter flow rate of a gas sample from the environment gas sensor(s) 30 on the basis of the identification/characterization of one or more accessory devices 200 of an accessory device assembly in fluid connection with inlet 38. In a number of embodiments, the control system is configured to adjust the speed of the pump to a first speed, which is different from or outside of the standard range of pump speed, to provide a response time of the one or more gas sensors within a range of predetermined sampling times (which may be shorter than a sampling time required for operation of the pump with the standard range of pump speed). In a number of embodiments, the control system adjusts/increases the speed of the pump to a first speed to provide a suitable wait time or sampling time which is approximately constant regardless of the accessory device(s) 200 identified to be attached to inlet 38 over a broad array of potential accessory device combinations. As used herein, a wait time or sampling time is a time required for the gas sample from the environment to reach sensor(s) 30, and for sensor(s) to provide an accurate response which is representative of the concentration of the one or more analytes in the sampled environment. In addition to decreasing sampling time and increasing efficiency as compared to current sampling practices, dynamically controlling/increasing flow rate to provide a sampling time within a predetermined range or a sampling time that is relatively constant can increase user confidence in accurate readings, reduce confusion, and reduce the likelihood of user error. In a number of embodiments, gas detection devices hereof may be configured to provide the user with an option to proceed in a sensing mode using the standard range of pump speed or to enter a sensing mode in which the pump speed is increased to decrease sampling time as described above. The user may be provided with the sampling time required if a standard range of pump speed is used.

As known in the gas detection device arts, the control system of device 10 may be configured to notify the user of a low power/battery state (for example, via display 46a or another indicator). If a lower power/battery state exists, the control system may, for example, prevent increasing of pump speed to reduce sample time as described above. Moreover, the control system may be configured to slow the pump speed to another speed, which may vary within a range of pump speed, which is reduced or slower than the standard range of pump speed. The control system may further be configured to determine a sampling time associated with the reduced or slower speed and provide that information to the user.

As set forth above, gas detection devices are currently calibrated at a calibration flow rate/pump speed which is used in operating the gas detection device. In a number of embodiments hereof, the control system of gas detection device 10 is configured to increase the speed of the at least one pump to the first speed, which may vary within a first range of speed, during transit of the sample to gas sensors 30 and to decrease the pump system to a second speed, which may vary within a second range of speed, during measurement of one or more responses of at least one of gas sensors 30. The second speed is, for example, equal to or approximately equal to the speed (or range of speed) of the at least one pump used during calibration of the one or more gas sensors with a test gas. Similarly, in cases in which pump speed is slowed to conserve battery power during transit of the sample to gas sensors 30, the control system may be configured to increase the pump speed to the second speed during measurement of one or more responses of at least one of gas sensors 30. Alternatively, gas detection device 10 and sensors 30 thereof may be calibrated with a test gas at a plurality of pump speeds. Calibration at multiple pump speeds/flow rates may, for example, enable accurate, calibrated measurement over a range of increased and decreased pumps speeds/flow rates, eliminating the requirement to alter pump speed to single calibrated speed/range of speeds during measurement.

The control system may also be configured to determine the pump speed at least in part based upon measured environmental conditions. In that regard, data of environmental conditions may affect flow of gas through the accessory device transport path. Such environmental conditions include, for example, humidity, temperature, pressure, and/or altitude. Data on environmental conditions, variables or parameters may, for example, be obtained from various sensors that may be incorporated in device 10 or transmitted to device 10 from another device of system 5 or from another source. Likewise, operational parameters such as back EMF, pressure, PWM parameters etc., measured upon startup of device 10 including a particular accessory device assembly may be used in controlling pump speed during sample measurement. Moreover, data of wear on the pump system may be tracked and input to the pump may be controlled based upon the state of the pump to achieve pump speed/flow rate ranges as described herein. Feedback of data on flow rate (or one or more variables from which flow rate may be determined; for example, flow rate may be calculated as a function of back EMF and pressure) may additionally or alternative be used to control pump speed.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A gas detection device for detection of one or more gas analytes in an environment, comprising:
    a housing comprising an inlet via which gas to be sampled from the environment enters the housing,
    a control system within the housing comprising a processor system and a memory system in communicative connection with the processor system,
    one or more gas sensors within the housing in fluid connection with the inlet and in communicative connection with the control system, wherein each of the one or more gas sensors is independently responsive to one of the one or more gas analytes, and
    a pump system in communicative connection with the control system and comprising at least one pump in fluid connection with the inlet and in fluid connection with the one or more gas sensors,
    wherein the control system is configured to control the pump system to control flow rate of gas from the environment through an accessory device assembly comprising one or more accessory devices in fluid connection with the inlet on the basis of data for the accessory device assembly in fluid connection with the inlet, wherein the one or more accessory devices are positioned external to the housing and provide a transport path between the environment and the inlet.

2. The gas detection device of claim 1 wherein the pump system is positioned within the housing.

3. The gas detection device of claim 1 further comprising a data transfer system in communicative connection with the control system via which the data for the accessory device assembly may be transmitted to the control system.

4. The gas detection device of claim 3 wherein the data transfer system is configured for at least one of manual entry of data for the accessory device assembly by a user or to receive data transmitted from at least one communication device associated with the accessory device assembly.

5. The gas detection device of claim 4 wherein an accessory device identification system is in communicative connection with the control system, the accessory device identification system comprising a database, the database having stored therein data for a plurality of accessory device assemblies, including reference identification data therefor, the accessory device identification system being configured to identify the accessory device assembly from identification data included in the data received via the data transfer system for the accessory device assembly in fluid connection with the inlet.

6. The gas detection device of claim 5 wherein the database is stored in the memory system of the control system and the database further has stored therein characterization data for the plurality of accessory device assemblies, the memory system further comprising one or more algorithms stored thereon and executable by the processor system to control the at least one pump to adjust speed of the at least one pump to alter flow rate of a gas sample from the environment to the one or more gas sensors on the basis of the identification of the accessory device assembly.

7. The gas detection device of claim 4 wherein the data entered manually includes characterization data for the accessory device assembly thereof and the memory system further comprises one or more algorithms stored thereon and executable by the processor system to control the at least one pump to adjust speed of the at least one pump to alter flow rate of a gas sample from the environment to the one or more gas sensors on the basis of the characterization data of the accessory device assembly in fluid connection with the inlet.

8. The gas detection device of claim 3 wherein the data transfer system is configured for manual entry of data for the accessory device assembly by a user and to receive data transmitted from at least one communication device associated with the accessory device assembly.

9. The gas detection device of claim 8 wherein the control system is configured to adjust the speed of the at least one pump to a first speed, which may vary within a first range of speed, to provide a sample time of the one or more gas sensors within a range of predetermined response times.

10. The gas detection device of claim 9 wherein the control system is configured to determine the first speed of the at least one pump such that the sample time of the one or more gas sensors is approximately a predetermined time regardless of the identification of the accessory device assembly in fluid connection with the inlet.

11. The gas detection device of claim 10 wherein the one or more gas sensors are calibrated with a test gas at a plurality of pump speeds.

12. The gas detection device of claim 9 wherein the control system is configured to increase the speed of the at least one pump to the first speed during transit of the gas sample to the one or more gas sensors and to decrease the speed of the at least one pump to a second speed, which may vary within a second range of speed, during measurement of one or more responses of at least one of the one or more gas sensors, the second speed being determined to achieve a flow rate approximately equal to a calibration flow rate of the at least one pump during calibration of the one or more gas sensors with a test gas.

13. The gas detection device of claim 12 wherein the control system is configured to determine the first speed at least in part based upon measured environmental conditions communicated to the control system via at least one of a sensor system of the gas detection device and a sensor system in communication with the gas detection device.

14. The gas detection device of claim 9 wherein the control system is configured to determine the first speed at least in part based upon data of measured environmental conditions communicated to the control system via at least one of a sensor system of the gas detection device and a sensor system in communication with the gas detection device.

15. The gas detection device of claim 3 wherein the control system is configured to adjust speed of the at least one pump to alter flow rate of a gas sample from the environment to the one or more gas sensors on the basis of the data for the accessory device assembly in fluid connection with the inlet.

16. A method of operating a gas detection device for detection of one or more gas analytes in an environment, the gas detection device including:
a housing comprising an inlet via which gas to be sampled from the environment enters the housing,
a control system within the housing comprising a processor system and a memory system in communicative connection with the processor system,
one or more gas sensors within the housing in fluid connection with the inlet and in communicative connection with the control system, wherein each of the one or more gas sensors is independently responsive to one of the one or more gas analytes, and
a pump system in communicative connection with the control system and comprising at least one pump in fluid connection with the inlet and in fluid connection with the one or more gas sensors,
the method, comprising: controlling flow rate of gas from the environment through an accessory device assembly comprising one or more accessory devices in fluid connection with the inlet via the control system on the basis of data for the accessory device assembly in fluid connection with the inlet, wherein the one or more accessory devices are positioned external to the housing and provide a transport path between the environment and the inlet.

17. The method of claim 16 wherein the pump system is positioned within the housing.

18. The method of claim 16 wherein the gas detection device further comprises a data transfer system in communicative connection with the control system via which the data for the accessory device assembly may be transmitted to the control system.

19. The method of claim 18 wherein the data transfer system is configured for at least one of (i) manual entry of data for the accessory device assembly by a user and (ii) to receive data transmitted from at least one communication device associated with the accessory device assembly, and the method further comprises operating the control system to adjust speed of the at least one pump to alter flow rate of a gas sample from the environment to the one or more gas sensors on the basis of the data for the accessory device assembly in fluid connection with the inlet.

20. A method of detecting one or more gas analytes in an environment, comprising: controlling flow rate of gas from the environment through an accessory device assembly comprising one or more accessory devices placed in fluid connection with an inlet of a housing of a gas detection device on the basis of data for the accessory device assembly received via a data transfer system of the gas detection device, the gas detection device further including one or more gas sensors within the housing and in fluid connection with the inlet, wherein each of the one or more gas sensors is independently responsive to one of the one or more gas analytes, wherein the accessory device assembly is positioned external to the housing and provides a transport path between the environment and the inlet.

* * * * *